(12) United States Patent
Egorov et al.

(10) Patent No.: US 6,645,377 B1
(45) Date of Patent: Nov. 11, 2003

(54) SYSTEMS FOR COLUMN-BASED SEPARATIONS, METHODS OF FORMING PACKED COLUMNS, AND METHODS OF PURIFYING SAMPLE COMPONENTS

(75) Inventors: Oleg B. Egorov, Richland, WA (US); Matthew J. O'Hara, Richland, WA (US); Jay W. Grate, West Richland, WA (US); Darrell P. Chandler, Richland, WA (US); Fred J. Brockman, Kennewick, WA (US); Cynthia J. Bruckner-Lea, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 123 days.

(21) Appl. No.: 09/620,408

(22) Filed: Jul. 20, 2000

Related U.S. Application Data

(60) Division of application No. 09/318,345, filed on May 25, 1999, now Pat. No. 6,136,197, which is a continuation-in-part of application No. 09/087,454, filed on May 27, 1998, now abandoned.

(51) Int. Cl.[7] .............................................. B01D 15/08
(52) U.S. Cl. ....................... 210/198.2; 210/659; 96/101
(58) Field of Search .................................. 210/635, 656, 210/657, 658, 659, 198.2; 95/82, 85; 96/101, 105, 107

(56) References Cited

U.S. PATENT DOCUMENTS

| | | | | |
|---|---|---|---|---|
| 2,708,519 A | * | 5/1955 | Novak | 210/198.2 |
| 4,042,499 A | * | 8/1977 | Ramstad | 210/198.2 |
| 4,070,284 A | * | 1/1978 | Fujita | 210/198.2 |
| 4,242,097 A | * | 12/1980 | Rich | 210/198.2 |
| 4,497,711 A | * | 2/1985 | Shepherd | 210/198.2 |
| 4,591,442 A | * | 5/1986 | Andrews | 210/198.2 |
| 4,676,898 A | * | 6/1987 | Saxena | 210/198.2 |
| 4,722,786 A | * | 2/1988 | Weaver | 210/198.2 |
| 4,840,730 A | * | 6/1989 | Saxena | 210/198.2 |
| 5,039,419 A | * | 8/1991 | Bradshaw | 210/198.2 |
| 5,234,586 A | * | 8/1993 | Afeyan | 210/198.2 |
| 5,630,943 A | * | 5/1997 | Grill | 210/198.2 |
| 5,667,676 A | * | 9/1997 | Alaska | 210/198.2 |
| 5,902,485 A | * | 5/1999 | Davis | 210/198.2 |
| 5,958,227 A | * | 9/1999 | Uematsu | 210/198.2 |
| 6,063,284 A | * | 5/2000 | Grill | 210/198.2 |

* cited by examiner

Primary Examiner—Ernest G. Therkorn
(74) Attorney, Agent, or Firm—Douglas E. McKinley, Jr.; Stephen R. May (57) ABSTRACT

The invention encompasses systems for column-based separations, methods of packing and unpacking columns and methods of separating components of samples. In one aspect, the invention includes a system for column-based separations, comprising:
  a) a fluid passageway, the fluid passageway comprising a column chamber and a flow path in fluid communication with the column chamber, the flow path being obstructed by a retaining material permeable to a carrier fluid and impermeable to a column matrix material suspended in the carrier fluid, the flow path extending through the column chamber and through the retaining material, the flow path being configured to form a packed column within the column chamber when a suspension of the fluid and the column matrix material is flowed along the flow path; and
  b) the fluid passageway extending through a valve intermediate the column chamber and the retaining material.

12 Claims, 9 Drawing Sheets

SYSTEMS FOR COLUMN-BASED SEPARATIONS, METHODS OF FORMING PACKED COLUMNS, AND METHODS OF PURIFYING SAMPLE COMPONENTS

CROSS REFERENCE TO RELATED APPLICATION

This patent application is a divisional application of Continuation-in-Part application Ser. No. 09/318,345, filed May 25, 1999, now U.S. Pat. No. 6,136,197, which was a Continuation-in-Part of application Ser. No. 09/087,454, filed May 27, 1998, now abandoned.

TECHNICAL FIELD

The invention pertains to systems for column-based separation, and to methods of forming and utilizing packed columns. In specific embodiments, the invention pertains to methods of separating sample components.

BACKGROUND OF THE INVENTION

Figure 1:
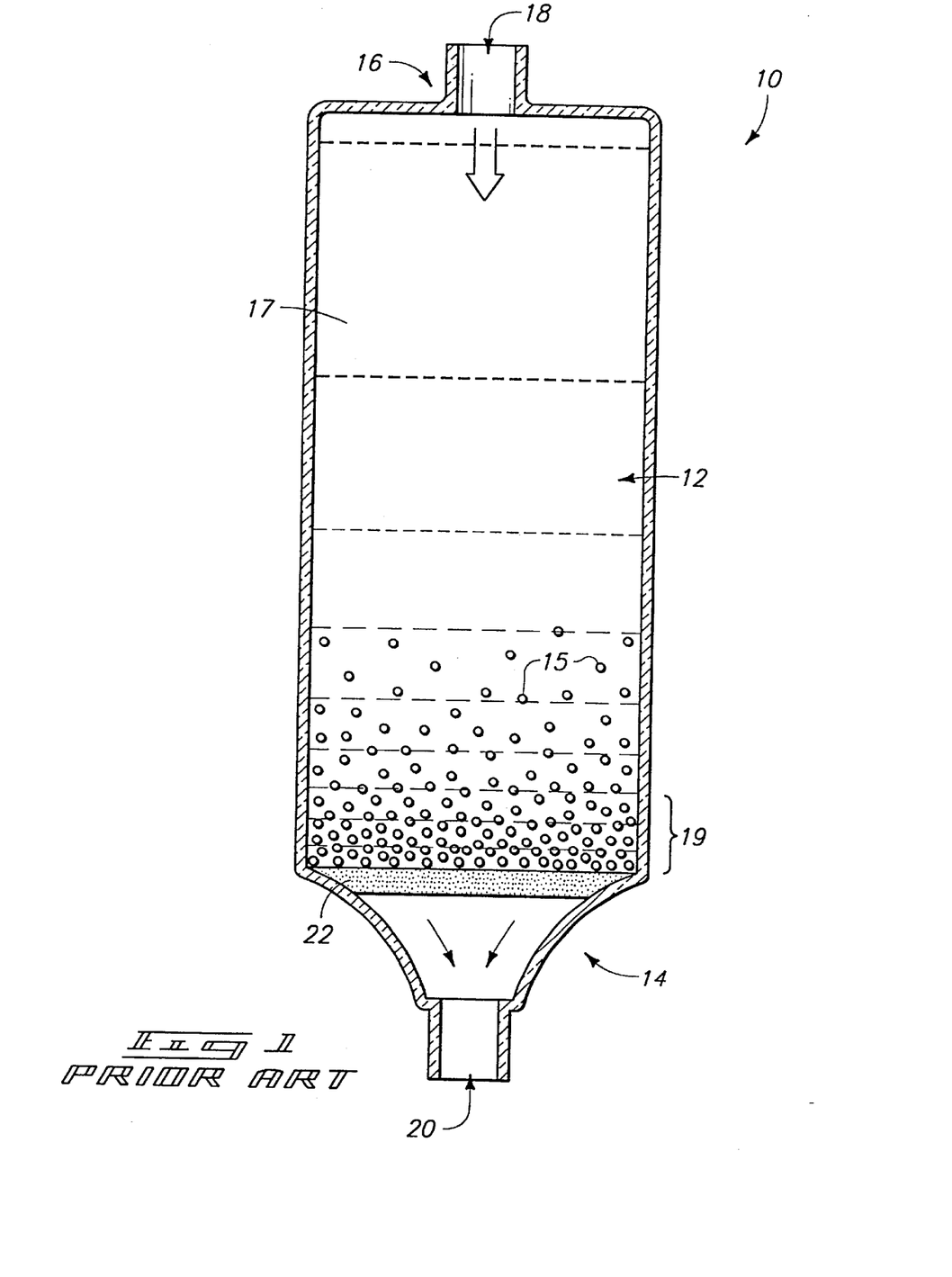
FIG. 1 is a diagrammatic, cross-sectional view of a prior art column construction.

Column-based separations are frequently used for selectively removing components from mixtures. A first step in utilizing column-based technology is to form a column. Such can be accomplished within a column chamber. An exemplary prior art column chamber 10 is illustrated in FIG. 1. Column chamber 10 comprises a longitudinal tubular section 12 having ends 14 and 16. An inlet 18 is provided at end 16, and an outlet 20 is provided at end 14. Outlet 20 is obstructed by a porous filter 22. Filter 22 can comprise, for example, a porous fritted glass or ceramic material.

A packed column is formed within chamber 10 by flowing a slurry comprising a mixture of matrix material 15 and carrier fluid 17 into inlet 18. Matrix material 15 comprises a plurality of particulates, such as, for example, beads. Filter 22 is permeable to the carrier fluid and impermeable to the matrix material. Accordingly, as the slurry is flowed into column chamber 10, matrix material 15 stacks against filter 22 to form a packed column 19 within tubular portion 12.

The composition of carrier fluid 17 and matrix material 15 vary depending on the components that are intended to be separated by the packed column, and on the mixtures (samples) within which such components are found. Example matrix materials are Sr-resin, TRU-resin, and TEVA-resin, all of which can be obtained from EIChrom Industries, Inc., of Darien, Ill. Such matrix materials can have particle sizes in the range of, for example, 20–100 micrometers. Sr-resin, TRU-resin, and TEVA-resin can be used for, for example, selectively retaining radioactive materials. Specifically, Sr-resin can selectively retain strontium, TRU-resin can selectively retain americium, and TEVA-resin can selectively retain technetium. Slurries utilized for forming packed columns of Sr-resin, TEVA-resin, or TRU-resin can comprise, for example, 0.074 gram/mL of Sr-resin in 3 M $HNO_3$; 0.142 grams/mL of TEVA-resin in 4 M $HNO_3$; or 0.076 grams/mL of TRU-resin in 0.1 M $HNO_3$, respectively.

Other materials that can be separated utilizing column-based systems are, for example, biological materials, such as nucleic acids. For instance, Tepnel Life Sciences sells polymeric micro-beads in diameters of approximately 60–100 micrometers which are covalently linked to specific oligonucleotide capture probes. Such micro-beads can be utilized for selective purification of nucleic acid fragments from a biological sample. For purposes of interpreting this disclosure and the claims that follow, the term "nucleic acid" is defined to include DNA nucleotides and RNA nucleotides, as well as any length polymer comprising DNA nucleotides or RNA nucleotides.

In addition to the above-discussed exemplary uses for column-based separations, numerous other applications for column-based separations are known to persons of ordinary skill in the art. The column-based separations generally have in common that a mixture in a first physical state (typically either a gas phase or a liquid phase) is flowed across a column matrix in a second physical state (typically either a liquid phase or a solid phase) to separate a component of the mixture from other materials of the mixture. Accordingly, the physical state of the matrix is generally different than the physical state of the component that is to be separated.

It can be desired to quantitate and/or otherwise analyze an amount of a component retained by a column matrix in a packed column. Accordingly, it can be desired to extract a retained component from a matrix materia. A method of extracting a retained component is to subject the column matrix to conditions which disrupt interactions between the matrix material and the component to thereby elute the component from the matrix material. In some applications, it is desirable to elute the retained material from the matrix material while the matrix material is still within a packed column, and in other applications it is desirable to remove the matrix material from, a packed column before eluting the retained component. Additionally, there are some applications in which it is desirable to remove a matrix material from a packed column and thereafter analyze the matrix material directly to quantitate and/or otherwise analyze an amount of a component retained on the matrix material.

A difficulty in utilizing column-based separations is in removing matrix material from a column chamber and subsequently repacking additional matrix material in the chamber to re-form a packed column. There are numerous reasons for removing matrix material from a chamber. For instance, a matrix material of a packed column can be rendered unusable after an initial separation, or after an initial series of separations. A matrix material can be rendered unusable if it is degraded by fluids passed through the material during a separation. Also, the matrix material can be rendered unusable if it becomes contaminated by materials within a sample because such contamination can pose a risk of cross-contamination.

For one or more of the above-discussed reasons, it is frequently desirable to repeatedly pack and unpack a column chamber with matrix material. Because packing and unpacking of column chambers is a time-consuming and laborious process, disposable columns are generally used. However, disposable columns still require labor for column changeout. Accordingly, it is desirable to develop new methods for packing and unpacking column chambers.

Figure 2:
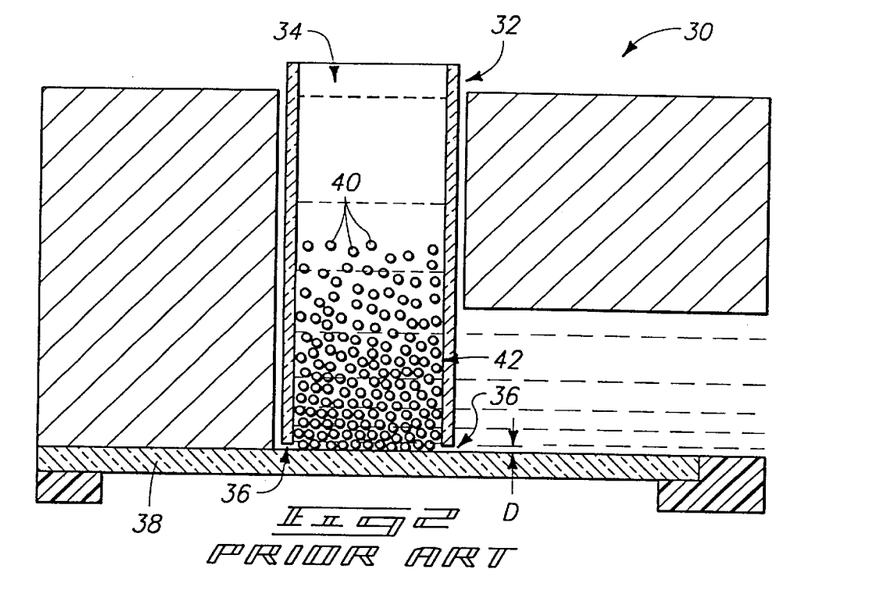
FIG. 2 is a diagrammatic, cross-sectional view of a prior art system for packing and unpacking a column chamber. The system of FIG. 2 is shown with the column chamber in a position for packing a matrix material within the column chamber.

A recent improvement is described with reference to an apparatus 30 in FIGS. 2 and 3. Referring to FIG. 2, apparatus 30 comprises a tubular column chamber 32 having an inlet end 34 and an outlet end 36. Outlet end 36 terminates proximate a plate 38. Plate 38 can comprise a window configured to enable light to pass through for spectroscopic measurement of materials eluting from column chamber 30. A matrix material 40 forms a packed column 42 within column chamber 32. Packed column 42 has a lateral periphery defined by tubular chamber 32. Packed column 42 can be formed by flowing a slurry of matrix material 40 and a carrier fluid into column chamber 32. Outlet end 36 of column chamber 32 is displaced from plate 38 by a distance "D" sufficient to enable the carrier fluid to pass between column chamber 32 and plate 38. However, the distance is less than an average width of matrix material 40. Accordingly, matrix material 40 is retained in column chamber 32 and stacks against plate 38 to form packed column 42.

Figure 3:
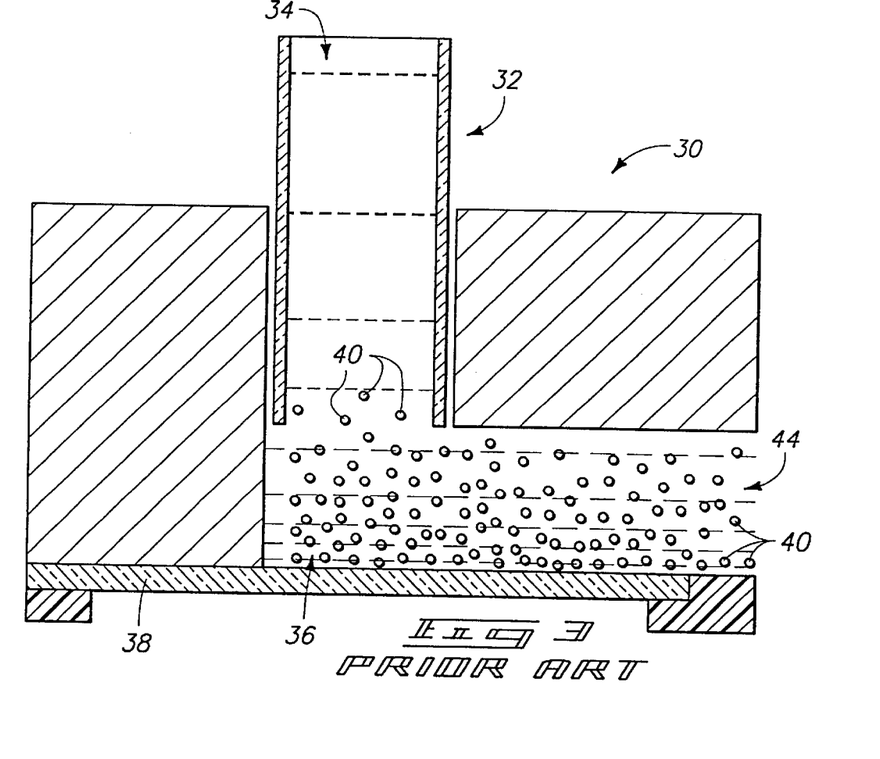
FIG. 3 is a view of the FIG. 2 system, with the column chamber shown in a position for unpacking the column chamber.

FIG. 3 illustrates a method for removal of matrix material 40 from packed column 42. Specifically, column chamber 32 is raised to enable matrix material 40 to pass beneath column chamber 32 and over plate 38. Subsequently, a fluid is flowed through chamber 32 to push matrix material 40 out of column chamber 32.

System 30 is improved relative to other methods of packing and unpacking columns in that it can provide a quick method for releasing packed column material from a column chamber, and can also provide a quick method for resetting the column chamber to be repacked with fresh matrix material. A difficulty with column system 30 is that it can be problematic to move an entirety of column chamber 32 during transitions between packing and unpacking operations. Further, precise tolerances are needed to hold beads and may leak beads. Discharged beads can undesirably pass through a detector. It can become increasingly difficult to move the entirety of column chamber 32 as a column-based separation is scaled up for larger operations. Accordingly, it is desirable to develop alternative methods for conveniently packing and unpacking column chambers, wherein a column chamber is not moved in transitioning between packing and unpacking operations.

SUMMARY OF THE INVENTION

In one aspect, the invention encompasses a method of packing and unpacking a column chamber. A matrix material is packed within a column chamber to form a packed column. After the packing, the matrix material is unpacked from the column chamber without moving the column chamber.

In another aspect, the invention encompasses a method of purifying a component of a sample. A column chamber having an inlet end and an outlet end is provided. The outlet end terminates proximate both a first flow, path and a second flow path. The first flow path is obstructed with a retaining material permeable to a first fluid and impermeable to a matrix material. The second flow path is blocked by a blocking material that removably blocks flow of both the first fluid and the column matrix material. A suspension of the first fluid and the matrix material is flowed into the column chamber and along the first flow path to form a packed column of the matrix material within the column chamber. The blocking material defines a portion of a periphery of the packed column. The matrix material is configured to selectively retain a component of the sample. The sample is flowed through the packed column and along the first flow path to separate the component from the rest of the sample. The blocking material is removed without moving the column chamber. After removing the blocking material, a second fluid is flowed through the column chamber and along .the second flow path to remove the matrix material from the column chamber.

In yet another aspect, the invention encompasses a system for column-based separations. The system comprises a fluid passageway containing a column chamber and a flow path in fluid communication with the column chamber. The flow path is obstructed by a retaining material permeable to a carrier fluid and impermeable to a column matrix material suspended in the carrier fluid. The flow path extends through the column chamber and through the retaining material. The flow path is configured to form a packed column within the column chamber when a suspension of the fluid and the column matrix material is flowed along the flow path. The column chamber defines a portion of a periphery configured to retain the packed column. Another portion of the periphery is defined by a blocking material that removably blocks flow of both the carrier fluid and the column matrix material. The blocking material is spaced from the packed column by a region configured to retain a fluid.

An advantage of the impermeable material is that the surface area of the material in contact with fluid is always in contact with fluid. In other words, there is no material surface area that alternately contacts fluid then, say an interior chamber surface. This feature minimizes the potential of sample to sample contamination since a sample may be completely washed through and not captured on an alternately or intermittently exposed surface. This is especially valuable for nucleic acid samples wherein one molecule of a previous nucleic acid sample can be detected in a subsequent nucleic acid sample.

BRIEF DESCRIPTION OF THE DRAWINGS

Preferred embodiments of the invention are described below with reference to the following accompanying drawings.

FIG. 6 is a view of the system in a position for packing the column chamber.

DETAILED DESCRIPTION OF THE PREFERRED EMBODIMENTS

Figure 6:
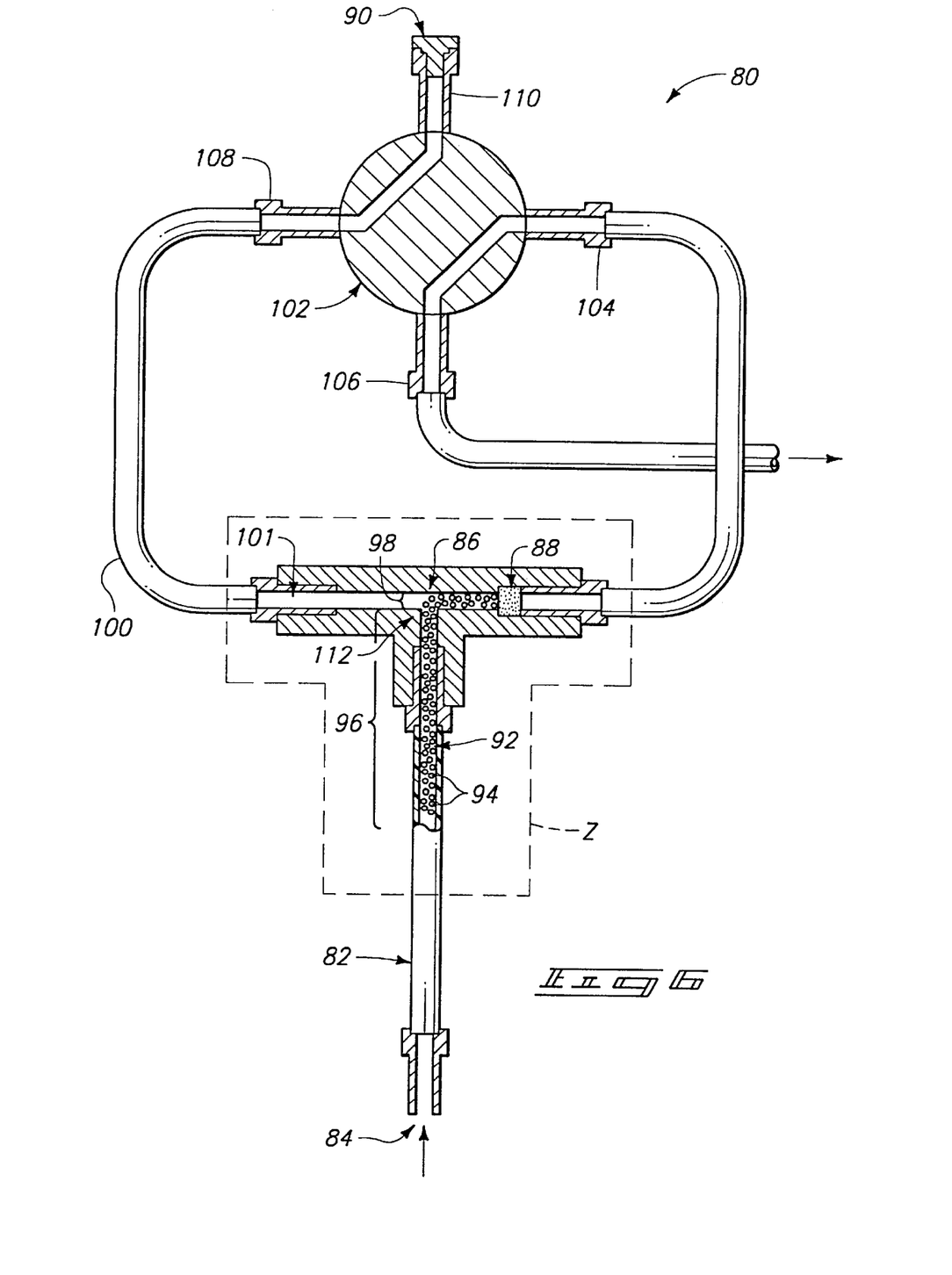
FIG. 6 is a view of a second embodiment system of the present invention for packing and unpacking a column chamber.
Figure 7:
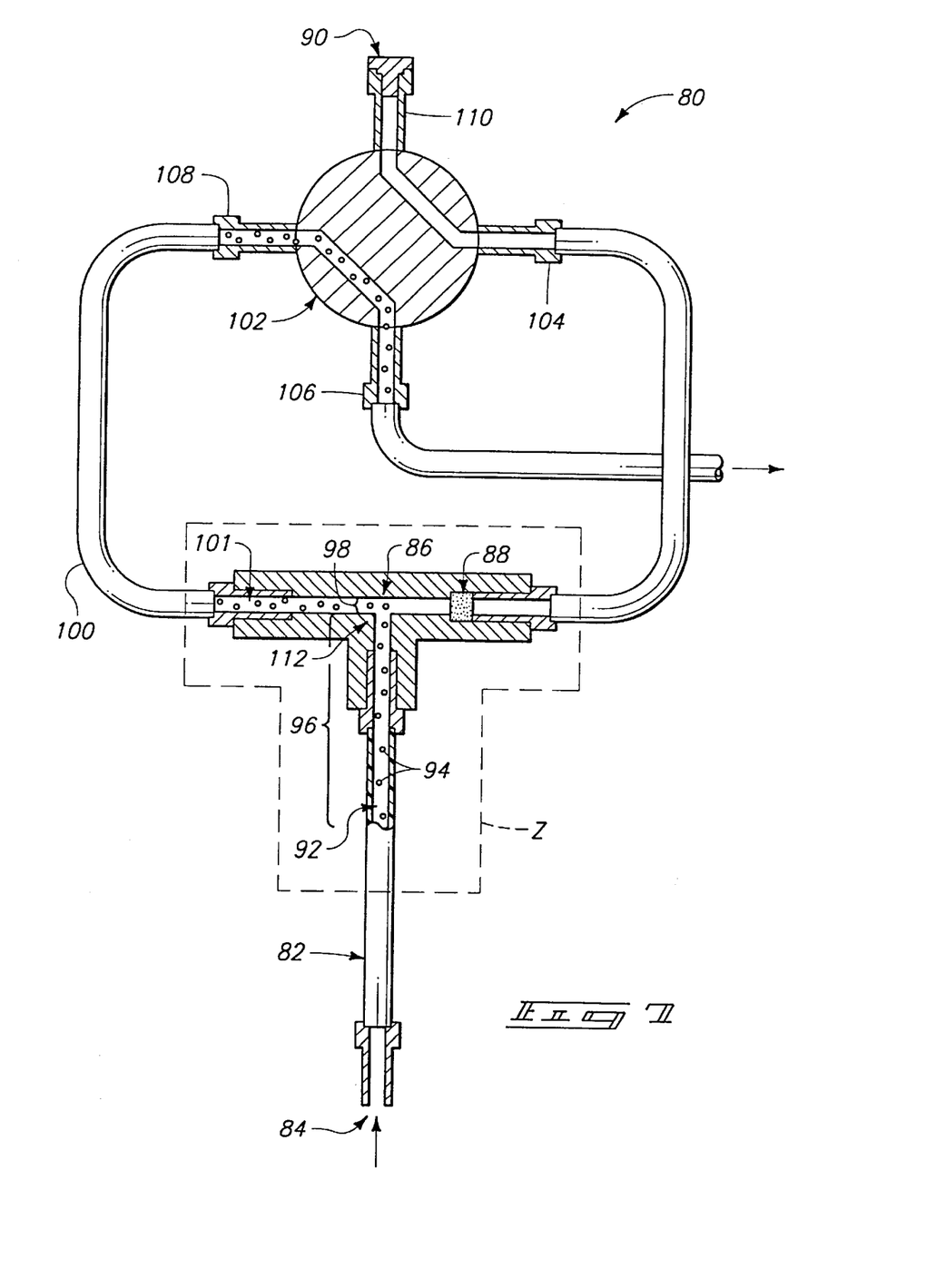
FIG. 7 is a view of the FIG. 6 system shown in a position for unpacking a column chamber.
Figure 8:
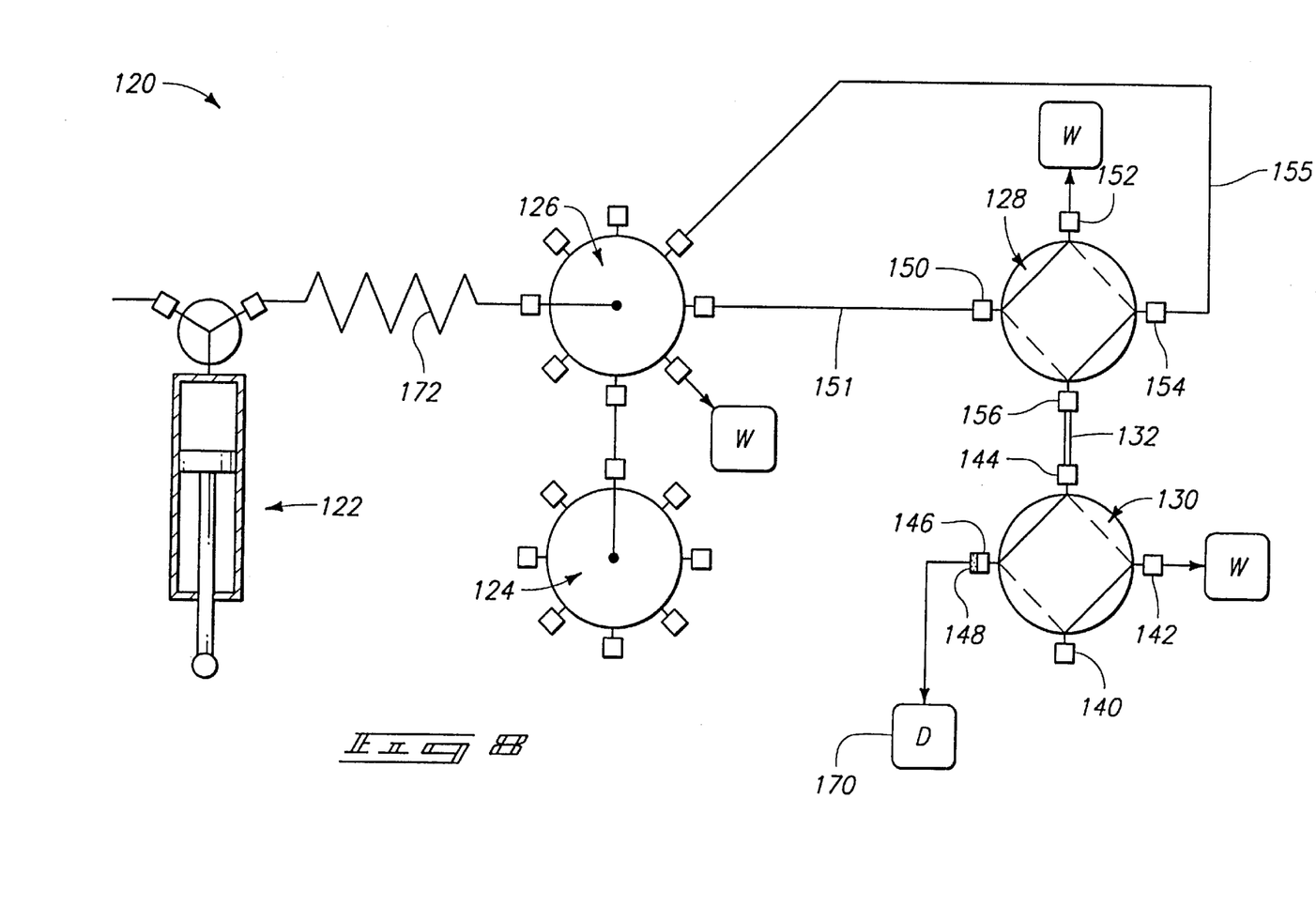
FIG. 8 is a schematic view of a first embodiment sample treatment apparatus of the present invention. The apparatus of FIG. 8 incorporates a third embodiment packing and unpacking system.

In one aspect, the invention encompasses systems for column-based separations configured to pack and unpack column chambers without moving the column chambers. Embodiments pertaining to this aspect of the invention are described with reference to FIGS. 4–8, with FIGS. 4 and 5 illustrating a first embodiment, FIGS. 6 and 7 illustrating a second embodiment, and FIG. 8 illustrating a third embodiment.

Figure 4:
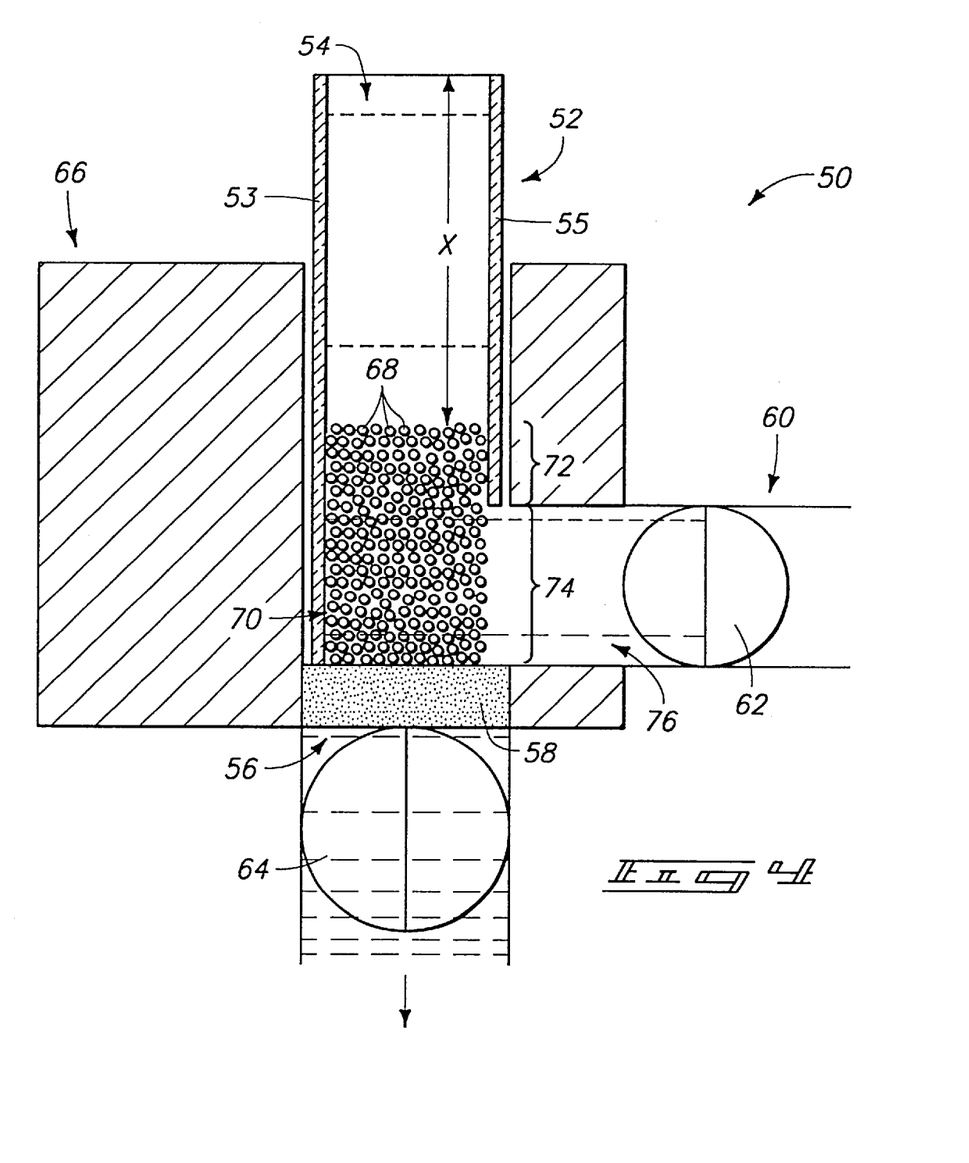
FIG. 4 is a diagrammatic, cross-sectional view of a first embodiment system of the present invention for packing and unpacking a column chamber. The system of FIG. 4 is shown in a position for packing a column chamber.
Figure 5:
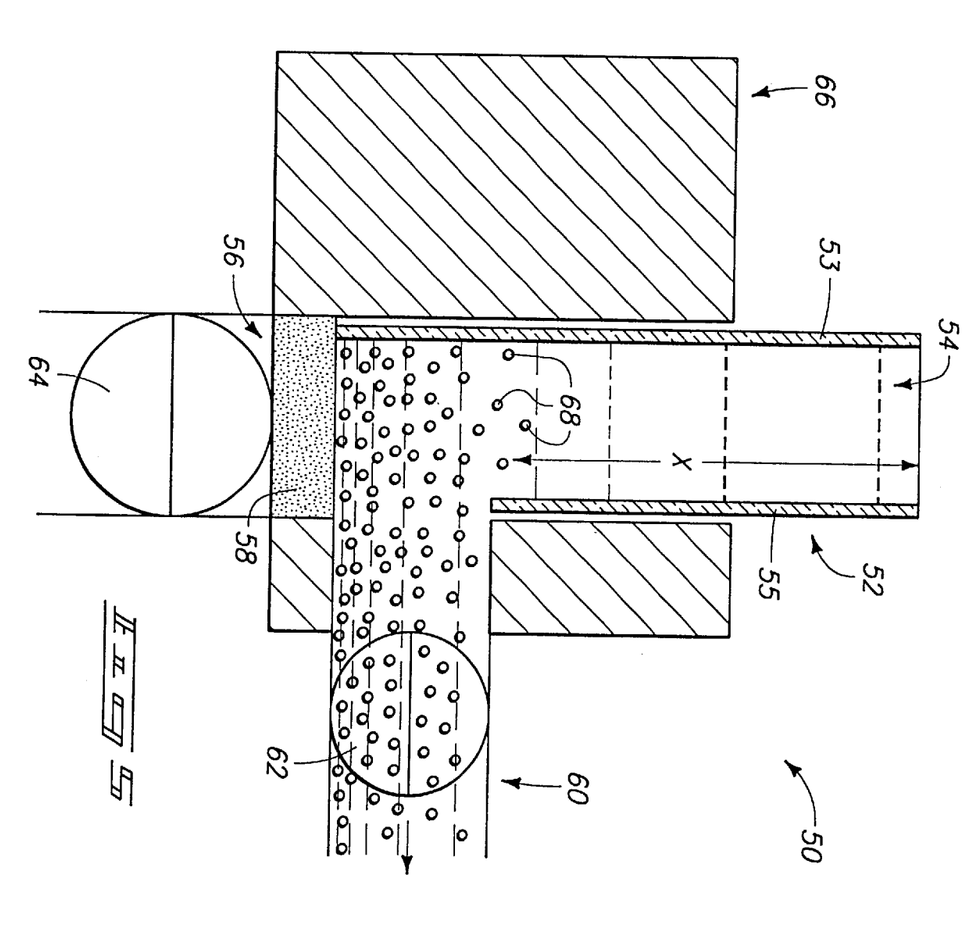
FIG. 5 is a view of the FIG. 4 system shown in a position for unpacking the column chamber.

Referring to FIGS. 4 and 5, a system 50 for column-based separations comprises a column chamber 52 having an inlet end 54 and an outlet end 56. Column chamber 52 comprises a longitudinal axis "X", and can be formed of, for example, glass, plastic or metal. In the shown cross-sectional sideview, column chamber 52 comprises a pair of opposing sidewalls 53 and 55. Although sidewalls 53 and 55 are shown as physically separated in the shown cross-sectional view, it is to be understood that sidewalls 53 and 55 can be portions of a continuous periphery. For instance, column chamber 52 can have a cylindrical shape, with sidewalls 53 and 55 forming portions of a continuous circular periphery of the cylinder.

Outlet end 56 is obstructed with a retaining material 58 which is permeable to a carrier fluid and impermeable to a column matrix material suspended in the carrier fluid. Retaining material 58 can comprise, for example, a porous fritted glass and/or ceramic material. A first flow path for fluids passing through column chamber 52 is defined to extend through retaining material 58. A first valve 64 is provided to selectively block flow along the first flow path. First valve 64 is shown in a "open" position in FIG. 4, enabling a fluid to flow along the first flow path.

System 50 further comprises a tube 60, which in the shown preferred embodiment extends to the longitudinal axis "X" of column chamber 52. It is further preferred that tube 60 extend at about a right angle to the longitudinal axis "X". A rotatable second valve 62 is provided within tube 60 to regulate flow of material through tube 60. Second valve 62 is configured to block flow of both fluids and matrix material. FIG. 4 illustrates system 50 with second valve 62 in a "closed" position to prevent flow of fluid and matrix material through tube 60. Tube 60 defines a second flow path for materials flowed into column chamber 52, and in FIG. 4 such second flow path is illustrated as being blocked by closed valve 62.

In the shown cross-sectional view, sidewall 53 terminates in a fluid tight seal at retaining material 58, and sidewall 55 terminates at a location elevationally displaced from retaining material 58. Second valve 62 is laterally displaced from column chamber 52 and can be used to regulate flow of materials under sidewall 55. Specifically, when valve 62 is in a closed position, flow under sidewall 55 is prevented, and when valve 62 is in an open position, flow under sidewall 55 is enabled.

A support structure 66 is provided to support column chamber 52 and tube 60. Support structure 66 can comprise, for example, a plastic material molded to fit column chamber 52 and tube 60. Alternatively, support structure 60 can comprise, for example, a clamp.

A matrix material 68 is provided within column chamber 52. In the FIG. 4 orientation of system 50, wherein valve 62 is in a closed position and valve 64 is in an open position, matrix material 68 is packed within column chamber 52 to form a packed column 70. Such packing encompasses flowing a slurry of matrix material and carrier fluid into chamber 52 and along the first flow path though retaining material 58. The carrier fluid penetrates retaining material 58 and exists column chamber 52, leaving matrix material 68 to stack against retaining material 58 and form packed column 70. During packing of matrix material 68, column chamber 52 defines a first portion 72 of a periphery configured to retain packed column 70, and closed valve 62 defines a second portion 74 of the periphery configured to retain packed column 70. Specifically, closed valve 62 defines second portion 74 through a retaining fluid 76 that is within a fluid-filled space extending between valve 62 and packed column 70. Retaining fluid 76 forms a boundary along which matrix material 68 is packed to form packed column 70. In the shown preferred embodiment, retaining fluid 76 forms a barrier which precludes matrix material 68 from entering the fluid-filled sp ace between valve 62 and packed column 70 47 during formation of packed column 70.

The retaining fluid 76 can be either a gas or a liquid, but is preferably a liquid. Also, the carrier fluid is preferably a liquid. In preferred methods of the present invention, tube 60 and column chamber 52 are initially filled with a first liquid prior to introduction of a slurry comprising a liquid carrier fluid and a matrix material within column chamber 52. The liquid carrier fluid then flows through outlet 56, while the first liquid remains within tube 60 to form a retaining fluid volume between valve 62 and packed column 70.

As packed column 70 is formed, a pressure may be exerted on retaining fluid 76 to elevate a pressure of retaining fluid 76 above one atmosphere. This can occur, for example, if pressure is utilized to force carrier fluid through retaining material 58.

Referring to FIG. 5, system 50 is illustrated with valve 64 in a closed position and valve 62 in an open position. Opening valve 62 unblocks flow of matrix material along tube 60, enabling discharge of matrix material 68 through tube 60. During discharge of matrix material 68, a fluid, preferably a liquid, is flowed through column chamber 52 and along the second flow path comprising tube 60 to flush matrix material 68 from column chamber 52. The fluid flowed during discharge of matrix 68 can be referred to as a dislodging fluid, and can be the same as one or both of the carrier fluid and the retaining fluid 76 (FIG. 4).

The system 50 described with reference to FIGS. 4 and 5 can be shifted from a packing mode to an unpacking mode by activating two valves. Specifically, when valve 62 is in a closed position and valve 64 is in an open position, system 50 is in a column chamber packing mode (FIG. 4), and when valve 62 is in an open position and valve 64 is in a closed position, system 50 is in a column chamber unpacking mode (FIG. 5). Thus, the embodiment of FIGS. 4 and 5 enables a system to be shifted from a column chamber packing mode to a column chamber unpacking mode without moving the column chamber.

Referring next to FIGS. 6 and 7, a second exemplary embodiment column system 80 is illustrated. FIG. 6 illustrates column system 80 in a column chamber packing mode, and FIG. 7 illustrates column system 80 in a column chamber unpacking mode. Referring first to FIG. 6, column system 80 comprises a column chamber 82 having an inlet end 84 and an outlet end 86. Outlet end 86 is obstructed with a retaining material 88 permeable to a carrier fluid, and impermeable to a matrix material. Retaining material 88 can comprise, for example, a porous glass or ceramic material.

System 80 further comprises a valve 102 having at least four ports and two positions. The four ports are labeled as 104, 106, 108, and 110. Port 110 is blocked with a blocking material 90. Ports 104 and 108 are in fluid communication with column chamber 82, and comprise a first flow path and a second flow path, respectively, from column chamber 82. Port 106 is an unblocked outlet port which can lead to, for example, a detector, a collection chamber, or additional equipment for processing substances eluted from packed column 92. Blocking material 90 is configured to block flow of both column matrix material and carrier fluid, and can comprise, for example, a plastic plug threadably inserted into port 110, or a suitable valve.

A packed column 92 of matrix material 94 is formed within column chamber 80. Column chamber 80 defines a portion 96 of a periphery of packed column 92, and blocking material 90 defines another portion 98 of the periphery of packed column 92. Blocking material 90 is separated from the periphery of packed column 92 by a fluid-filled region 100 filled with a retaining fluid 101. Fluid-filled region 100 can comprise, for example, a plastic tubing.

In the shown embodiment, column chamber 82 comprises a right-angle bend 112 proximate retaining material 88, and accordingly proximate an outlet extending through material 88. The portion 98 of the periphery of packed column 92 defined by the retaining fluid 101 is at right-angle bend 112.

An alternative method of describing the apparatus of system 80 is to describe column chamber 82 as comprising a longitudinal section terminating at right-angle bend 112, and further comprising a fluid filled region 100 comprising a tube at right angle bend 112. In the shown embodiment, the longitudinal section of column chamber 82, together with right-angle bend 112, and the tubular portion of fluid filled region 100 that joins with right-angle 112 define a "T" shape in a zone illustrated as zone "Z".

Referring to FIG. 7, system 80 is shown with valve 102 moved into second position which couples port 104 with blocked port 110 and which couples port 108 with open port 106. The second position of valve 102 thus blocks the first flow path through retaining material 88 and opens the second flow path adjacent column chamber 82 to enable discharge of matrix material 94 from column chamber 82.

The above-discussed embodiments of FIGS. 4–7 can enable a column chamber to be packed and unpacked without moving the column chamber. The embodiments utilize a blocking material (either valve 62 or material 90) to removably block flow of fluids and column matrix material from a column chamber. When flow is blocked, the column chamber can be packed with a matrix material, and when the flow is unblocked the column chamber can be unpacked.

The column chambers of FIGS. 4–7 are preferably packed and unpacked with matrix material while flowing fluids through the column chambers in an identical flow direction during both the packing and unpacking operations. Specifically, all, or at least most, of the matrix material is preferably expelled from a column chamber along an identical flow direction as was utilized to pack the column chamber. However, it is to be understood that the invention also encompasses embodiments in which flow of fluid through a column chamber is reversed during a packing or unpacking operation. Preferably, the flow during a packing operation will not be reversed, but will instead be continuous in a flow direction from an inlet of the column chamber through a retaining material (such as retaining material 88 of FIGS. 6 and 7). Also preferably, a flow of fluid through a column chamber will be predominately in a single direction from an inlet of the column through an outlet of the column during an unpacking operation. However, the unpacking operation can preferably also comprise some sporadic instances wherein flow is reversed (i.e., to go from an outlet to an inlet) to assist in dislodging matrix material from within column chamber 82, and to assist in removing matrix material embedded within a porous retaining material (such as retaining material 88 of FIGS. 6 and 7) that could otherwise potentially clog the retaining material.

Embodiments of the present invention can be operated with a vast number of matrix materials, as will be appreciated by persons of ordinary skill in the art. Example matrix materials are the Sr-resin, TRU-resin, and TEVA-resin described above in the "Background" section of this disclosure, which can be utilized for separating compounds comprising radioactive atoms from other materials in a sample. Additional example matrix materials including but not limited to glass, sepharose, polystyrene, Tepnel, Qiagen, zirconium, hydroxyapatite, POROS, PEG-PS, and PS the last three of which are made by PerSeptive are materials suitable for separating biological materials. Certain matrix materials are materials for separating nucleotide fragments (e.g., nucleic acid, DNA, RNA or combinations thereof) based upon a sequence of the fragments, such as, for example, the Tepnel micro-beads discussed above in the "Background" section of this disclosure. Biological materials include but are not limited to viruses, cells for example prokaryote, eukaryote and combinations thereof.

Figure 9:
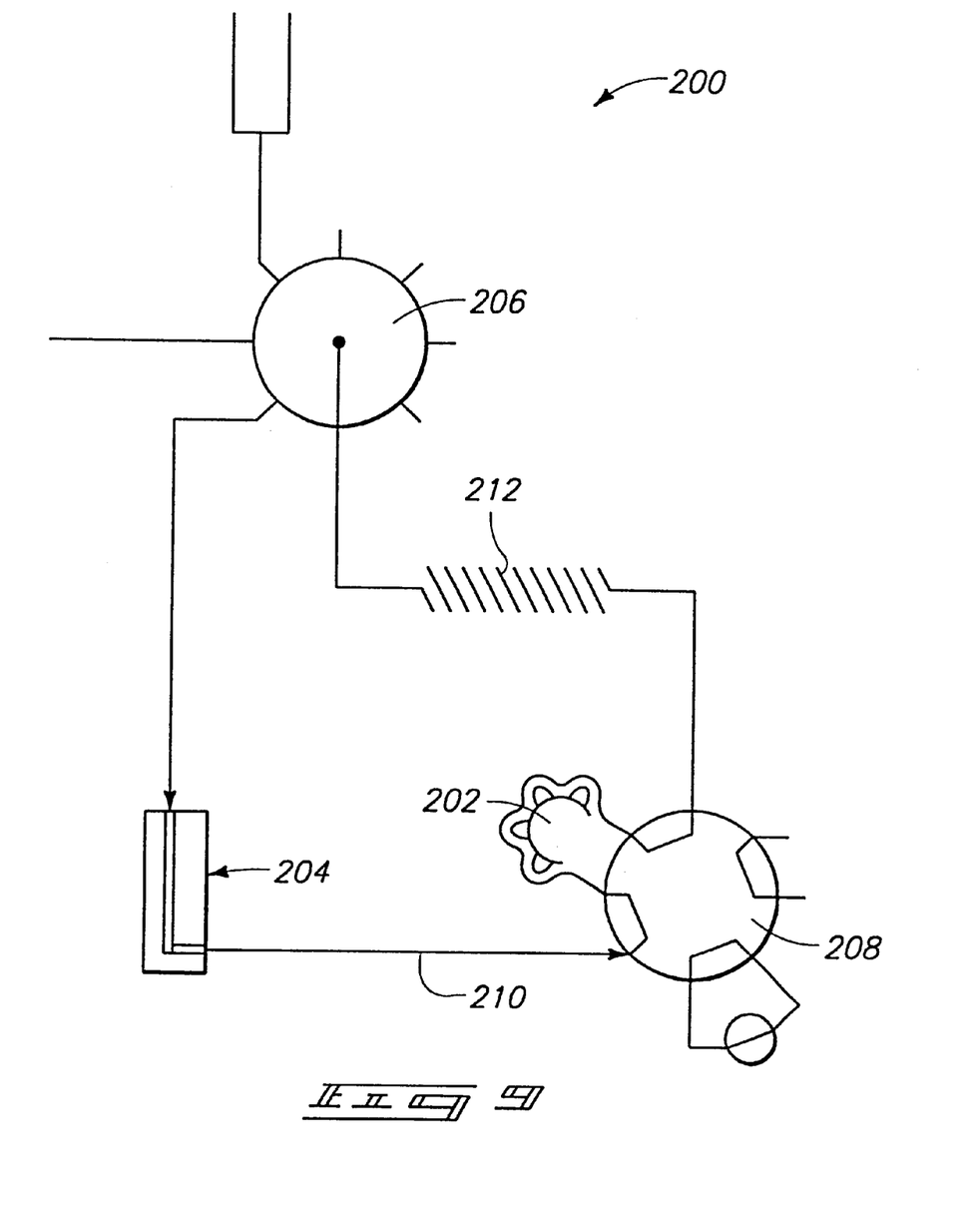
FIG. 9 is a schematic view of a second embodiment sample treatment apparatus of the present invention.

Column systems of the present invention can be incorporated into methods for purifying components of samples. Example purification apparatuses are shown in FIGS. 8 and 9, with FIG. 8 showing a first embodiment apparatus and FIG. 9 showing a second embodiment apparatus.

Referring to FIG. 8, a purification apparatus 120 comprises a pump 122 (for example, a syringe pump), valves 124, 126, 128 and 130, and a column chamber 132. Exemplary valves 128 and 130 are 4 port, 2 position diverter valves such as may be obtained from, for example, Valco as Cheminert valves. Valve 130 comprises ports 140, 142, 144 and 146, with port 146 obstructed by a filter 148. Filter 148 can comprise, for example, a 25 μm poresize polypropylene column end frit with a 5 mm diameter, and can be placed into a port of a 2 position diverter valve with a flat-bottom chromatographic fitting. Column chamber 132 is packed by flowing a slurry of carrier fluid and matrix material into column chamber 132 while a fluid flow is coupled through ports 144 and 146. Filter 148 is permeable to the carrier fluid and impermeable to the matrix material. Column chamber 132 can be subsequently unpacked by activating valve 130 to couple a fluid flow through ports 144 and 142. Port 142 is preferably an open port sized to permit flow of a slurry comprising matrix material through port 142. Column chamber 132 and valve 130 together comprise a third embodiment column system of the present invention that can be packed and unpacked without moving a column chamber.

Valve 128 comprises ports 150, 152, 154 and 156. Port 152 can lead to, for example, a waste reservoir (labeled "W"). Port 150 is preferably in fluid communication with a wide dimension tubing 151, such as, for example, tubing having an internal diameter of 1.6 mm, to enable a slurry comprising matrix material and carrier solution to easily flow through the wide bore tubing during packing of column 32. Port 154 is preferably in fluid communication with tubing 155 having a relatively narrow bore, such as, for example, an internal diameter of 0.8 mm. Such narrow bore tubing enables a sample to be flowed onto column 32 with less dilution of the sample than would occur with a wider diameter tubing. In operation, a fluid flow is coupled through ports 150 and 156 during packing of column 32, and a fluid flow is coupled through ports 154 and 156 during loading of a sample onto column 152. Either of ports 154 or 150 can be coupled to port 156 during elution of sample from matrix material of column 132. A sample eluted from the matrix material of column 132 can be passed through filter 148 to a detector 170 downstream of port 146. Detector 170 can comprise, for example, a polymerase chain reaction (PCR) machine.

Valves 126 and 124 are utilized for providing reagents, samples, and slurries to column 132. Preferably, if a slurry is to be provided to column 132, it is first flowed into tubing segment. 172, that can be any shape. Tubing segment 172 is preferably coiled as shown to save space. The slurry subsequently flow from tubing segment 172 to column 132. By flowing the slurry to tubing segment 172, the slurry can be provided within apparatus 120 without introduction of gas bubbles into the tubing of the apparatus. Specifically, tubing segment 172 can be filled with a liquid (preferably a liquid inert to reaction with the slurry) prior to injection of slurry into holding coil 172. The slurry can then be injected into tubing segment 172 to displace the liquid. To prevent mixing of the injected slurry with the displaced liquid, a small air bubble (about 100 microliters) can be introduced into tubing segment 172 prior to injecting the slurry.

Each of valves 126, 128 and 130 preferably comprises a port going to a waste material reservoir "W". Example dimensions of various items of apparatus 120 are as follows: column 132 can comprise a volume of about 250 μL, holding coil 172 can comprise a void volume of about 12 mL, and syringe pump 122 can comprise a displacement of about 10 mL. A typical time for packing a 250 microliter column 132 is less than four and one-half minutes. The holding coil, column chamber and tubing of apparatus 120 can comprise, for example, TEFLON™, with the holding coil and tubing preferably comprising FEP(fluorinated ethylene propylene)-TEFLON and the column chamber preferably comprising PTFE(polytetrafluoroethylene)-TEFLON. Example conditions for utilizing apparatus 120 are described in Tables 1–5.

TABLE 1

Automated Protocol For Renewable Sorbent Column Packing (Described With Reference To The Apparatus Of FIG. 8)

| Step # | Event (Flow Rate) |
|---|---|
| 1. | switch two-position valves 128 and 130 to positions 2, and 1, respectively |
| 2. | aspirate 100 μL of air into the holding coil (15 mL/min) |
| 3. | aspirate 635 μL of carrier into a syringe (35 mL/min) |
| 4. | aspirate 700 μL of sorbent slurry into the holding coil (3 mL/min) |
| 5. | dispense 700 μL of sorbent slurry to renewable column via a packing line (3 mL/min) |
| 6. | repeat steps 4 and 5 as necessary[a] |
| 7. | dispense 635 μL to the packing line (3 mL/min). Pause 12 seconds. |
| 8. | switch two-position valve 128 to position 1. |
| 9. | aspirate 100 μL of air into the holding coil (15 mL/min) |
| 10. | aspirate 750 μL of carrier into a syringe (35 mL/min) |
| 11. | dispense 700 μL through the slurry delivery line to the waste line (6 mL/min) |
| 12. | aspirate 100 μL of air into the holding coil (15 mL/min) |
| 13. | aspirate 750 μL of 50% ethanol solution into the holding coil (15 mL/min) |
| 14. | aspirate 1.8 mL of carrier into the syringe (35 mL/min) |
| 15. | empty syringe through the slurry delivery line to waste (10 mL/min) |

[a]steps 3 and 4 were executed 3 times to pack Sr-resin and TRU-resin columns, and 2 times to pack TEVA-resin column.

TABLE 2

Automated Protocol for Sorbent Bed Disposal (Described With Reference To The Apparatus Of FIG. 8)

| Step # | Event (Flow Rate) |
|---|---|
| 1. | switch two-position valves 130 and 130 to positions 2 |
| 2. | aspirate 350 μL through the column body and slurry delivery line (10 mL/min) |
| 3. | aspirate 100 μL of air into holding coil (15 mL/min) |
| 4. | aspirate 4.25 mL of carrier into syringe (35 mL/min) |

TABLE 2-continued

Automated Protocol for Sorbent Bed Disposal (Described With Reference To The Apparatus Of FIG. 8)

| Step # | Event (Flow Rate) |
|---|---|
| 5. | switch two-way valve 130 to position 1 |
| 6. | aspirate 100 μL through the column body and packing line (10 mL/min) |
| 7. | switch two-way valve 130 to position 2 |
| 8. | dispense 900 μL through the column body to waste (10 mL/min) |
| 9. | switch two-way valve 130 to position 1 |
| 10. | aspirate 100 μL through the column body (10 mL/min) |
| 11. | switch two-way valve 130 to position 2 |
| 12. | aspirate 100 μL of air into the holding coil (15 mL/min) |
| 13. | dispense 1.5 mL through the slurry line and column body to waste (10 mL/min) |
| 14. | switch two-way valve 130 to position 1 |
| 15. | aspirate 100 μL of air into the holding coil (15 mL/min) |
| 16. | aspirate 1.2 mL of 50% ethanol solution into the holding coil (10 mL/min) |
| 17. | dispense 2.6 mL through the slurry delivery line and column body to waste (10 mL/min) |

TABLE 3

Automated Reagent Delivery Sequence for $^{90}$Sr Separation[a,b]

| Step # | Description: Reagent (Flow Rate) |
|---|---|
| 1. | pack Sr-resin column |
| 2. | condition column: 1.5 mL 8M $HNO_3$–0.12M HF (1 mL/min) |
| 3. | load sample/wash column: 150 μL 8M $HNO_3$–0.12M HF/100 μL sample/6 mL 8M $HNO_3$–0.12M HF (0.5 mL/min or 1 mL/min) |
| 4. | elute Sr: 5 mL 0.05M $HNO_3$–0.12M HF (0.5 mL/min) |
| 5. | expel Sr-resin sorbent |

[a]The sample zone in step 3 is sequenced between 8M $HNO_3$–0.12M HF eluent zones; aspiration sequence: 6 mL eluent 8M $HNO_3$–0.12M HF/100 μL sample/150 μL eluent.
[b]The flow rate in step #3 was 1 mL/min for the analysis of some nuclear waste samples.

TABLE 4

Automated Reagent Delivery Sequence for Am Separation[a]

| Step # | Description: Reagent (Flow Rate) |
|---|---|
| 1. | pack TRU-resin column |
| 2. | condition column; 1.5 mL 2M $HNO_3$ (1.0 mL/min) |
| 3. | load sample/wash column: 100 μL sample/6 mL 2M $HNO_3$ (1.0 mL/min) |
| 4. | elute Am: 4 mL 3M HCl (1.0 mL/min) |
| 5. | elute actinides: 4 mL 0.1M ammonium bioxalate (1 mL/min) |
| 6. | expel TRU-resin sorbent |

[a]bioxalate elution step #5 was omitted during analysis of some nuclear waste samples

TABLE 5

Automated Reagent Delivery Sequent for $^{99}$Tc Separation

| Step# | Description: Reagent (Flow Rate) |
|---|---|
| 1. | pack TEVA-resin column |
| 2. | condition column: 1.5 mL 0.5 M $HNO_3$-12 M HF (0.5 mL/min) |
| 3. | load sample: 400 μL sample solution (0.5 mL/min) |
| 4. | wash column: 5 mL 0.5 M $HNO_3$-12 M HF (0.5 mL/min) |
| 5. | wash column: 1.5 mL deionized water (0.5 mL/min) |
| 6. | expel TEVA-resin sorbent and collect in vial |

Referring next to FIG. 9, a second embodiment sample purification apparatus 200 comprises a pump 202 (such as a shown peristaltic pump), a column system 204, and valves 206 and 208. Column system 204 can comprise, for example, one of the above-discussed first, second or third embodiment column systems of the present invention. Column system 204 is shown with a single outlet 210 which can, for example, correspond to a single outlet from outlet port 106 of system 80 (FIGS. 7 and 8), or can correspond to a joined outlet formed from joining the first and second flow paths of system 50 (FIG. 4) in an embodiment of system 50 which is not shown.

Apparatus 200 further comprises a holding coil 212 configured for holding either a sample which is to be separated with column system 204, or a slurry which is to be utilized for forming a packed column. Apparatus 200 can have particular application for separating components of biological samples. For instance, a desired component of a biological sample will frequently be present to a small concentration in a large sample. Apparatus 200 permits the sample to be repeatedly cycled across column system 204, which can increase an amount of a biological component ultimately bound, to a packed column relative to an amount which would be bound if a sample were not cycled multiple times across column system 204.

EXAMPLE 1

Experiments were conducted to demonstrate radiological separations using the apparatus and method of the present invention. The apparatus used was as described above as the third embodiment. Automated protocols for column packing and unpacking are described above in Table 1 and Table 2. In an example method the column system in FIG. 8 was used to perform analytical separation and determination of $^{90}$Sr in nuclear waste samples using Sr-resin. An on-line liquid scintillation detector was used to observe eluting peaks. The sample was loaded on the column in strong nitric acid solution (>3 M concentration), where Sr ions were strongly and nearly selectively retained. The matrix and most interfering radioactive ions, including the $^{90}$Y daughter, showed no retention and were removed with a strong nitric acid wash. Strontium was then eluted using a dilute nitric acid solution (ca. 0.05 M). The protocol for implementing the separation is shown above in Table 3. Reagent solution of 8 M HNO$_3$-0.12 M HF was used as a column wash to ensure removal of the tetravalent actinides which were coretained with $^{90}$Sr.

The experimental procedure listed in Table 3 was applied to a high activity $^{90}$Sr/$^{90}$Y standard (2.14×10$^5$ $^{90}$Sr dpm/mL in 2 M HNO$_3$) in triplicate, the separation flow rate was 0.5 mL/min. For triplicate runs on standards, both net peak area and peak maximum counts were reproducible within a 2 s counting error (3% and 9% respectively). The separated Sr fractions from the standard runs were collected and counted off-line to estimate the on-line detection efficiency (Ed) and separation recovery (E$_s$). The $^{90}$Sr separation recovery, E$_s$, was 92±2%, and the on-line detection efficiency, E$_d$, was 62±3%. Reuse of Sr-resin generally requires additional column wash steps in order to reduce strontium carryover into the subsequent analysis. A reagent blank run using a conventional chromatographic column performed immediately after the separation of a high activity $^{90}$Sr standard indicated carryover of ~7%. However, no carryover was evident if the reagent blank run following the analysis of the high-activity standard was performed on the automatically repacked column. No carryover was detected using a more sensitive off-line liquid scintillation analysis of a collected Sr fraction (less than 0.07% carry-over).

Consequently, one of the primary benefits of using renewable column technique demonstrated is that analyte carryover into succeeding analyses due to retention on column material is eliminated. Lengthy column clean-up steps and blank runs, which are sometimes required when reusing sorbent extraction columns, were unnecessary when using the renewable column.

The renewable column apparatus shown in FIG. 8 was applied to separation of $^{241}$Am from nuclear waste sample for determination by alpha-spectroscopy using TRU-resin. Determination of $^{241}$Am in nuclear waste samples using alpha-spectroscopy requires that Am is separated from the stable matrix, highly radioactive fission products, and potential radioactive interferences (e.g., $^{238}$Pu). The procedure given in Table 4 was applied to a dissolved vitrified glass nuclear waste sample prepared in 2 M HNO$_3$-0.05 M NaNO$_2$. The sample was spiked with 5.0×10$^5$ dpm/mL of $^{241}$Am and $^{239}$Pu. On-line radioactivity detection was used to monitor the separation. The ammonium bioxalate elution step is required if the TRU-resin column is to be reused for subsequent Am separations. However, using the renewable column technique, the sorbent column can be automatically repacked after the Am elution step. In this case, there was no need to elute the actinides still present on the column (Table 4, step 5). Additional column wash steps to reduce potential carryover into subsequent analysis were also eliminated. The separation time was reduced and mixed waste generation was minimized. This separation approach was applied towards the analysis of nuclear waste samples with off-line detection by alpha spectrometry. Analytical results were in close agreement with those obtained by standard manual protocols.

Renewable column technique was used to for separation and analysis of $^{99}$Tc in nuclear waste samples using TEVA-resin. The automated protocol listed above in Table 5 was developed to pack and condition TEVA-resin column, load the sample, and perform the column wash that removes stable matrix and radioactive interferences (e.g., $^{137}$Cs and $^{90}$Sr/$^{90}$Y). Eluent comprising 0.05 M HNO$_3$-0.12 M HF reagent was used as a wash to eliminate retention of the teravalent Pu. The same reagent was used to perform Sr elution as described earlier. Residual nitric acid present on the column after the column wash step was removed using 1.5 mL of water (Table 5, step 5). After the sample load and column wash steps (Table 5), the TEVA-resin sorbent was expelled from the system. The sorbent slurry in water (3 mL) was collected into a vial, mixed with 15 mL of scintillation cocktail and analyzed off-line by liquid scintillation spectrometry.

The following samples (1 mL aliquots of 0.1 M HNO$_3$ solutions) were analyzed using the SI-RSC separation format: 1) reagent blank, 2) tank waste sample; 3) tank waste sample spiked with 2300 dpm/mL $^{99}$Tc(VII), and 4) tank waste sample spiked with 4350 dpm/mL of $^{99}$Tc(VII). Blank subtracted detector count rate (cpm) plotted for the sample and two spiked samples against the added standard activity (dpm) gave a straight line (cpm=0.937 dpm +358, R=1.000). The sample $^{99}$Tc activity was determined from the x-axis intercept of the standard addition plot. The detection efficiency for the heterogeneous TEVA-resin slurry/scintillation cocktail samples was estimated to be 95±4%. The separation recovery was quantitative (99±5%). The analysis result (±2 s, corrected for dilutions) for a tank waste sample obtained using the SI-RSC technique was 1240±163 dpm/mL. This is in satisfactory agreement with the value of 1121±146 dpm/mL determined by standard analysis procedures. These results demonstrated a unique capability of the described technique to perform automated separations that require recovery of spent sorbent for subsequent analytical steps.

EXAMPLE 2

DNA Purification from Soil Extracts

DNA Extraction Procedure

Figure 10:
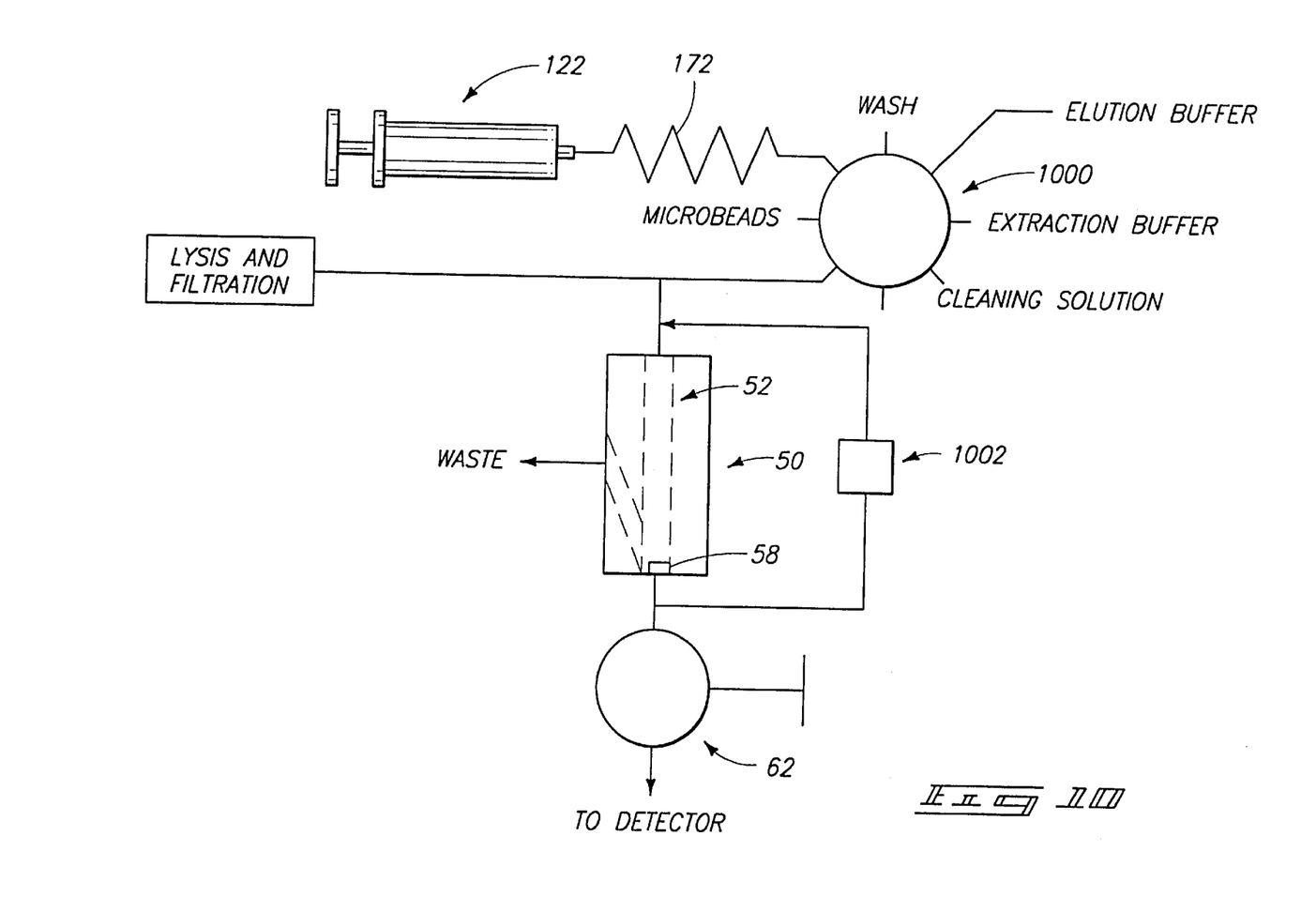
FIG. 10 is a schematic view of another embodiment of the present invention.

This example demonstrates the utility of the renewable microcolumn for DNA purification from complex samples. This example includes 60 µm particles with DNA binding sites, however any DNA binding particles ranging in size from about 10 µm to 200 µm could be used with this procedure for DNA purification. A schematic of the system used for these experiments is shown in FIG. 10. The microcolumn 50 was machined from Plexiglass to include a 1.8 mm diameter column 52. The column included a PEEK frit 58 with a 10 µm pore size (Upchurch). A syringe pump 122 (Cavro) was used for single pass experiments, and an Eldex reciprocating pump 1002 was added for recirculating the sample through the column 52. An eight port valve 1000 was used to direct flow of solutions. A typical analytical protocol is outlined in Table E2-1.

TABLE E2-1

| Procedural Step | Solution Composition | Solution volume | Flowrate |
|---|---|---|---|
| Add Column | 15 mg/ml Tepnel 1392r beads in 0.3 M NaCl | To produce 7 µl packed bed volume | 3 µl/s |
| Inject Sample | 1 ng or 100 ng Geobacter chapellii DNA in 0.3 M NaCl (or soil extract) (DNA concentration is $8.3 \times 10^{-13}$ M or $8.3 \times 10^{-15}$ M) | 200 µl | 0.9 µl/s |
| Rinse Column | 0.3 M NaCl | 80 µl | 3 µl/s |
| Wash Column | 0.5X SSC (0.075 M NaCl, 0.0075 M NaCitrate) | 1700 µl | 3 µl/s |
| Elute DNA | Water | 100 µl | 0.3 µl/s |

Summary of the Automated DNA Sample Processing Procedure Used for Extraction of *Geobacter chapellii* DNA Spiked Into Clean Solutions and Crude Soil Extracts.

Tepnel microbeads derivatized with universal 1392r oligonucleotide were used for the purification. The flowrates for sample injection and DNA elution are average flowrates produced by alternating flow at 3 µl/s and stopped flow. After the DNA is eluted, the column is automated flushed from the system.

The microbeads for DNA purification were obtained from Tepnel Life Sciences (Cheshire, England) and included universal 16S rDNA oligonucleotide 1392r with a $dT_8$ linker covalently attached to 60 µm microbeads. The binding capacity was estimated to be 2 pmol $mg^{-1}$ (or $cm^2$) beads ($1.27 \times 10^{12}$ capture probes $mg^{-1}$) based upon a competitive hot/cold assay using complementary oligonucleotides (Tepnel). Underivatized beads were also obtained to test for non-specific binding of nucleic acids. Before experimenting with Tepnel reagents in the fluidic system, we performed batch capture experiments using both underivatized and 1392r-derivatized microbeads.

For each nucleic acid size and quantity, automated capture experiments were performed with 200 µl blank extract (no DNA), purified *G. chapellii* genomic DNA in 0.3M NaCl, and at least two replicate captures of *G. chapellii* genomic DNA in 200 µl soil extract. The sample processing times for the primary separation events are shown in Table E2-2. The nucleic acid capture program was initiated by delivering the affinity matrix from a stirred slurry (15 mg $ml^{-1}$ in 0.3 M NaCl) to the renewable column, resulting in a 7 µl bed volume (1.6 mm ID×3.5 mm column height) containing approximately 3.7 mg bead material, 3.5 $cm^2$ surface area and $4.4 \times 10^{12}$ capture probes.

TABLE E2-2

DNA Extraction Summary: Sample Processing Time

| | 1 pass automated | 10 pass automated | batch manual |
|---|---|---|---|
| sample contact time (flowrate) | 3 min 6 sec (0.93 µl/s) | 11 min 7 sec (3 µl/s) | 240 min |
| total hybridization time[a] | 3.5 min | 19 min | 240 min |
| rinse time (flowrate) | 9 min (3 µl/s) | 9 min (3 µl/s) | 10 min[b] |
| elution time | 5.5 min | 5.5 min | 10 min[b] |
| total processing time | 18 min | 33.5 min | 260 min |

Comparison of processing times from DNA sample introduction to DNA elution. Processing times are summarized for 1 pass of DNA through the renewable column, 10 passes (recirculation) of the DNA sample, and a manual batch reaction using the same reagents. In all cases the sample volume was 200 µl, and the elution volume was 100 µl. Processing times in the automated system were not optimized for speed, and therefore do not necessarily reflect a lower limit on processing speed within the system and for other sample matrices.
[a]Total hybridization time is the sample contact time plus the time elapsed during column washing with the hybridization solution (0.3 M NaCl).
[b]Approximately 20 minutes are required to manually wash/collect microbeads and elute DNA in batch, using a standard 3 x 0.5 ml bead rinse protocol.

[a]Total hybridization time is the sample contact time plus the time elapsed during column washing with the hybridization solution (0.3 M NaCl).
[b]Approximately 20 minutes are required to manually wash/collect microbeads and elute DNA in batch, using a standard 3×0.5 ml bead rinse protocol.

Comparison of processing times from DNA sample introduction to DNA elution. Processing times are summarized for 1 pass of DNA through the renewable column, 10 passes (recirculation) of the DNA sample, and a manual batch reaction using the same reagents. In all cases the sample volume was 200 µl, and the elution volume was 100 µl. Processing times in the automated system were not optimized for speed, and therefore do not necessarily reflect a lower limit on processing speed within the system and for other sample matrices.

Nucleic acid extracts (200 µl) were heat denatured at 100° C. for 10 min., quick-chilled on ice and perfused over the microcolumn at 0.9 µl $sec^{-1}$ for a total contact time of approximately 3 min. The unbound flow-through was collected for subsequent analysis. Beads were washed by perfusing with 80 µl 0.3M NaCl to remove the nucleic acid extract, and bound nucleic acids were washed in 1.7 ml 0.5×SSC (3 µl $sec^{-1}$), and hybridized target was eluted with 100 µl water at room temperature with a 5.5 min contact time. The total sample processing time from injection to elution was 18 minutes. The experimental conditions were identical for the 10 pass sample recirculation experiments, except the extract and hybridization solutions were recirculated 10 times over the column at a flow rate of 3 µl $s^{-1}$, resulting in a sample contact time of approximately 11 minutes instead of 3 minutes, and a total hybridization time of 19 minutes (Table E2-2). Eluted nucleic acids were lyophilized to dryness and resuspended in 20 µl water prior to PCR detection. Between captures, the flow system was washed extensively with a sequence of 0.16% Roccal microbial disinfectant, 10% bleach, and water.

PCR Amplification and Measurement of Capture Efficiency

Geobacter 16S rDNA and total eubacterial 16S rDNA were detected and enumerated using dilution-to-extinction PCR to estimate capture efficiency and, for captures in soil extracts, to provide a functional assay for DNA purity that cannot be obtained by scintillation counting of radiolabeled DNA. Estimates of capture efficiency were calculated by (PCR detection limit)×(dilution factor)×(conversion factor to account for entire eluant). For example, with a 64 copy detection limit, $5^3$ dilution to the last positive PCR signal, and a 2 $\mu$l DNA input into the 5-fold dilution series (10% of the total recovered DNA), $8 \times 10^4$ copies of DNA were recovered. At 1 ng input DNA ($1 \times 10^6$ copies of target, assuming one 16S rDNA copy per genome), the capture efficiency is therefore $(8 \times 10^4/1 \times 10^6) \times 100$, or 8%. Capture efficiencies calculated in this manner are conservative estimates and underestimate the actual capture efficiency. That is, the true extinction point of the PCR lies between the last positive signal and the next dilution in the 5-fold series. Further, the positive control used to calibrate the enumeration was non-fragmented, highly purified DNA rather than sheared DNA isolated from a soil extract (which may amplify with lower efficiency than the standard). These variables bias the calculation of capture efficiency downward, such that the actual capture efficiency calculated in the example above is >8% but <40%.

Purified DNA was serial diluted in a 5-fold series immediately prior to PCR. PCR primers were synthesized by Keystone Labs (Camarillo, Calif.): Gbc.1300f and Gbc.1400r; S-d401F-20, and S-d683aR-20; universal eubacterial primers fD1 and rP2. For both sets of Geobacter-specific primers, PCR reactions were carried out in 25 $\mu$l total volume, utilizing a Perkin-Elmer (Foster City, Calif.) 9600 thermal cycler and 0.2 ml thin-walled reaction tubes. Final reaction conditions were 2 $\mu$l purified DNA (or dilutions thereof), 10 mM Tris pH 8.3, 50 mM KCl, 2.5 mM $MgCl_2$, 200 $\mu$M each dNTP, 0.2 $\mu$M each primer, and 0.625 U Taq polymerase (Perkin Elmer) which had been pretreated with TaqStart™ antibody at 0.5× the recommended concentration (Sigma, St. Louis, Mo.). Assembled reactions were heated to 80° C. for 5 min (hot start) and amplifications were conducted by performing 5 cycles at 94° C. for 40 s, 60° C. for 10 s, 72° C. for 75 sec followed by 40 cycles at 94° C. for 12 s, 65° C. for 10 s, 72° C. for 80 s with a 2 s extension per cycle. A final 20 min, 72° C. extension was performed before chilling reactions to 4° C. Control reactions included no template, solution blank and system washes (pre-and post-capture), affinity-purified nucleic acids (i.e. system eluant) spiked with 250 fg G. chapellii genomic DNA, and a dilution series of G. chapellii genomic DNA. PCR conditions for universal eubacterial primers fD1/rP2 were essentially identical, except we utilized 1.5 mM $MgCl_2$ and a thermal profile consisting of 5 cycles at 94° C. for 40 s, 55° C. for 10 s, 72° C. for 75 sec, 30 cycles at 94° C. for 12 s, 65° C. for 10 s, 72° C. for 80 s, with a 2 s extension per cycle, and a 20 min, 72° C. final extension.

DNA Purification Results

Relative to batch capture protocols, the automated capture was faster (18 versus 260 minutes total processing time (Table E2-2) and resulted in an extraction efficiency that was equivalent to or better than that obtained in batch solution using the same reagents. The best batch capture efficiency was only 2% using 100 ng of 4–10 Kb DNA and a hybridization time of 240 minutes, and <0.4% for a 30 minute hybridization. Automated capture of the same DNA size fraction and concentration resulted in an extraction efficiency of 6.25%, with a single pass through the column and a hybridization time of 3.5 minutes.

DNA capture with one pass over the renewable affinity column varied appreciably as a function of target size and absolute target concentration as seen in Table E2-3. At 1 ng of input genomic DNA (ca. $10^6$ copies or 1.7 attamoles target), capture efficiency declined with the smaller DNA fragment sizes; for 100 ng genomic DNA inputs (ca. $10^8$ copies or 170 attamoles target), capture efficiencies were relatively constant and represented the highest observed capture efficiencies (6–30%). PCR analysis of the sample flow-through, column eluent and spent microbeads showed that the majority of DNA applied to the column could be detected in the flow-through fraction, indicating that significant amounts of DNA were not adsorbed by the fluidics system (tubing, valves) and detectable target DNA was not retained on the microbeads after elution. Automated capture of 1 Kb sheared DNA after 10 passes (ca. 19 min. hybridization time) over the microcolumn showed no improvement relative to single-pass experiments, suggesting that the capture efficiency was not limited by column contact time alone.

TABLE E2-3

| | | Genomic DNA added | | | |
|---|---|---|---|---|---|
| | | 4–10 Kbp Sheared | 1 Kbp Sheared | 0.5 Kbp Sheared | No DNA added |
| 1 ng | Clean Background | 8% | 1.6% | 0.3% | 0% |
| | Soil Background | 0.3% | 0.3% | 0.3% | 0% (0.04%) |
| 100 ng | Clean Background | 6% | 31% | 6% | 0% |
| | Soil Background | 0.3% (0.1%) | 0.3% (0.1%) | 0.002% (1%) | 0% (0.3%) |

Capture efficiency of *Geobacter chapellii* 16S rDNA with the Tepnel-1392r reagent and one pass through the renewable affinity column. Each value is the average of at least two capture experiments. 1 ng of *G. chapellii* genomic DNA =$10^6$ cell equivalents (1 fg cell$^{-1}$) or $10^6$ copies of target assuming 1 copy per cell. The estimated DNA content of the soil extract background was 3 $\mu$g per capture, or ca. $3 \times 10^9$ competitive DNA targets assuming 5 fg cell$^{-1}$ and one 16S rDNA target per fg. Values in parentheses indicate capture efficiency of total 16S rDNA target based on dilution-to-extinction PCR using universal 16S rDNA primers fd1/rP2. Further, the maximal amount of target DNA recovered from 1 ng genomic DNA captures was ca. 80 pg (ca. $8 \times 10^4$ copies), whereas the amount of target DNA recovered from the 100 ng genomic captures was 6–30 ng ($6 \times 10^6$–$3 \times 10^7$ copies). Therefore, the limited capture of 1 ng target at all size ranges was not due to surface saturation of available binding sites, suggesting that kinetic and/or thermodynamic effects limited nucleic acid capture at the lower target concentrations.

The capture efficiency for competitive eubacterial 16S rDNA from unspiked soil extract was 0.3%, similar to the capture efficiency of Geobacter genomic DNA targets that were also spiked into the soil background (Table E2-3). At both 1 ng and 100 ng of 4–10 Kb and 1 Kb DNA inputs into the soil background, the *G. chapellii* 16S rDNA specific capture and total eubacterial 16S rDNA capture were constant and of similar magnitude (0.3% capture efficiency), even though 100 ng of *G. chapellii* target constituted ca. 3% of the total 16S rDNA and 1 ng represented only 0.03% of total 16S rDNA target. These results indicate that the spiked DNA (up to $10^8$ additional targets) did not appreciably change the availability or binding efficiency of Geobacter targets relative to total, eubacterial, competitive 16S rDNA targets, and that humic acids did not bias the affinity binding for or against the added Geobacter DNA relative to indigenous 16S rDNA. In addition, these results indicate that the competitive DNA background did not bias the affinity capture system for or against low-copy genomic DNA targets (Geobacter 16S rDNA) in solution. However, the binding of competitive 16S rDNA sequences to the 1392r microbeads or non-specific binding of humic acids precluded more efficient binding of Geobacter target DNA, since purified Geobacter DNA was captured with up to 30% efficiency (at 100 ng) whereas Geobacter targets spiked into a soil background (at 100 ng) were captured with 0.3% efficiency.

These results demonstrate that the renewable microcolumn can be used to automate the purification of nucleic acids contained in complex samples such as a crude soil extract. The protocol can include passing the sample only one time over the column or recirculating the sample many times over the column. The extraction efficiency obtained using the automated system was equal to or better than the manual extraction efficiency using the same reagent. DNA (1 ng or 100 ng) in a soil extract was detectable by PCR after a single pass over the microcolumn using the automated system and only 18 minutes total processing time. This processing time was not optimized for speed, so does not necessarily reflect a lower limit on processing speed within the system and for other sample matrices. Although the capture efficiency using this reagent was not high, the purified DNA sample does not inhibit PCR detection. Without DNA purification prior to PCR, the DNA in the soil extract cannot be detected using PCR because of PCR inhibition by constituents of the soil extract. The automated renewable microcolumn system could also be used with other purification resins that bind DNA, or resins that bind other biomolecules, cells, or chemicals.

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

What is claimed is:

1. A column-based separations system comprising:
    a column chamber having an inlet and an outlet, said inlet capable of receiving a flow of a matrix material and a flow of a sample in a uniform direction and said outlet in fluid communication with a first flow path obstructed by a porous retaining material permeable to a carrier fluid and impermeable to a matrix material, the first flow path extending through a valve port controlling fluid flow through the retaining material; and
    a second flow path in fluid communication with the fluid outlet, said second flow path extending through a second valve port controlling flow of said matrix material.

2. The system of claim 1 wherein:
    said column chamber comprises in cross-sectional sideview a pair of opposing sidewalls; said retaining material blocking the outlet, one of the opposing sidewalls terminating in a fluid-tight seal at the retaining material, the other of the sidewalls terminating at a location elevationally displaced from the retaining material; and
    the second valve port extending to a valve that is laterally displaced from the column chamber, the valve having a closed position and an open position, the valve in the closed position substantially preventing fluid and matrix material flow under the other of the sidewalls, the valve in the open position enabling fluid and matrix material to flow under the other of the sidewalls.

3. The system of claim 1 wherein a valve having at least 2 positions and at least 4 ports includes said first and second valve ports.

4. The system of claim 1 comprising:
    said column chamber defining a portion of a periphery configured to retain a packed column, another portion of the periphery defined by a blocking material that removably blocks flow of both the carrier fluid and the matrix material, the blocking material spaced from the packed column by a region configured to retain a fluid.

5. The system of claim 4 wherein a valve having at least 2 positions and at least 4 ports includes said first and second valve ports, and wherein the blocking material is connected to the column chamber through the valve, a first of the at least two positions coupling the blocking material with the column chamber to block flow of the matrix material from the column chamber, a second of the at least two positions uncoupling the blocking material from the column chamber to remove the portion of the periphery defined by the blocking material and thereby permit flow of the matrix material from the column chamber.

6. The system of claim 1 wherein the column chamber comprises a periphery configured to retain the matrix material, a portion of the periphery being defined by a retaining fluid.

7. The system of claim 6 wherein the column chamber comprises a bend proximate the outlet, and wherein the portion of the periphery defined by the retaining fluid is at the bend.

8. The system of claim 6 wherein the retaining fluid is in a liquid state.

9. The system of claim 6 wherein said retaining fluid is constrained by a blocking material that removably blocks flow of both a carrier fluid and the matrix material, the blocking material being spaced from the packed column by a fluid-filled region.

10. The system of claim 9 wherein the column chamber comprises a longitudinal section and a bend, the bend being proximate the outlet, wherein the fluid-filled region is a tube at the bend.

11. The system of claim 10 wherein the longitudinal section, tube and bend together define a "T" shape.

12. The system of claim 9 further comprising:
    a pair of flow paths into the inlet, a first of the pair of flow paths comprising first tubing and a second of the pair of flow paths comprising second tubing, the first tubing having a larger internal diameter opening than the second tubing.

* * * * *